United States Patent [19]

Holladay et al.

[11] Patent Number: 4,784,483
[45] Date of Patent: Nov. 15, 1988

[54] BRIGHTNESS ACUITY TESTER

[75] Inventors: Jack T. Holladay, Houston, Tex.; Morey H. Waltuck, Sharon, Mass.

[73] Assignee: Mentor O & O, Inc., Norwell, Mass.

[21] Appl. No.: 846,626

[22] Filed: Apr. 1, 1986

[51] Int. Cl.$^4$ .................... A61B 3/02; A61B 3/10
[52] U.S. Cl. .................... 351/243; 351/272; 351/221
[58] Field of Search ............ 351/222, 237, 243, 233; 357/246, 244, 245, 221

[56] References Cited

U.S. PATENT DOCUMENTS

| | | | |
|---|---|---|---|
| 2,209,728 | 7/1940 | Higley | 351/243 X |
| 2,471,652 | 5/1949 | Papritz | 351/226 |

FOREIGN PATENT DOCUMENTS 1088456  3/1955  France .................... 351/223

*Primary Examiner*—Rodney B. Bovernick
*Attorney, Agent, or Firm*—Morse, Altman, Dacey & Benson

[57] ABSTRACT

A brightness acuity tester to assess functional visual acuity in bright light conditions and to test for recovery of visual activity after photostressing the retina is disclosed. The tester essentially comprises a device closed in one direction and open in an opposite direction, an aperture provided in the device, a source of illumination mounted within the device, a plug designed removably to be positioned in the aperture to seal the same, and a power source coupled to the source of illumination via a switch. Preferably, the source of illumination is provided with anintensity control and the power source with a voltage regulator. Preferably, the device comprises a reflector having diffusely reflecting characteristics. Preferably, the power source is a battery, making the tester a hand-held one.

22 Claims, 2 Drawing Sheets

BRIGHTNESS ACUITY TESTER

BACKGROUND OF THE INVENTION

1. Field of the Invention

The present invention relates generally to eye testers and, more particularly, to a brightness acuity tester to assess functional visual acuity in bright light conditions and to test for recovery of visual acuity after photostressing the retina.

2. The Prior Art

Clinical practicioners have long been aware of the disparity occurring between outdoor functional vision in bright light conditions and that measured in a standard dark refracting lane. Significant disparities usually occur with ocular media opacities, including corneal scars, lenticular opacities happening in anterior subcapsular, posterior subcapsular and nuclear sclerotic cataracts, posterior capsular opacification following cataract surgery, and vitreous opacities including a dense central floater or asteroid hyalosis. As for photostressing the retina, patients with maculopathies, such as cystoid macular edema, central serous choroidopathy and senile macular degeneration evince markedly prolonged recovery from photostress.

Presently, only inaccurate methods are available to the practicioner for testing a patient's visual acuity in bright light conditions and for photostressing the retina to test for subsequent recovery of visual acuity. These present day methods include: taking the patient outside into bright sunlight or at least adjacent an undraped window exposed to bright sunlight; holding a light source, such as a penlight, adjacent the patient's eye; or placing a bright light source near a test chart. None of these methods is accurate, repeatable or employs consistent brightness or is particularly desirable. They are used simply for want of a better system.

SUMMARY OF THE INVENTION

It is a principal object of the present invention to overcome the above disadvantages by providing a brightness acuity tester for assessing functional visual acuity in bright light conditions and to test for recovery of visual acuity after photostressing the entire mecular region with consistent brightness.

More specifically, it is an object of the present invention to provide a brightness acuity tester essentially comprising a device closed in one direction and open in an opposite direction, a viewing aperture provided in the device, a source of illumination mounted within the device, an occluding member designed removably to be positioned in the aperture to seal the same, and a power source coupled to the source of illumination via an "on" and "off" switch. Preferably, the source of illumination is provided with means to vary the intensity of the source of illumination. Preferably, the power source is provided with means to keep the voltage level to the source of illumination constant regardless of variations in the power source. Preferably, the device comprises a reflector having diffusely reflecting characteristics. Preferably, the power source comprises one or more batteries incorporated in a convenient handle attached to the device, rendering the same portable and hand-held. Preferably, the handle is formed at an angle so as to facilitate the holding of the device in close proximity to a patient's eye.

Other objects of the present invention will in part be obvious and will in part appear hereinafter.

The invention accordingly comprises the brightness acuity tester of the present disclosure, its components, parts and their interrelationships, the scope of which will be indicated in the appended claims.

BRIEF DESCRIPTION OF THE DRAWINGS

For a fuller understanding of the nature and objects of the present invention, reference is to be made to the following detailed description, which is to be taken in connection with the accompanying drawings, wherein:

FIGS. 2-9 are views similar to FIG. 1 but showing different embodiments thereof;

DETAILED DESCRIPTION OF THE PREFERRED EMBODIMENTS

Figure 1:
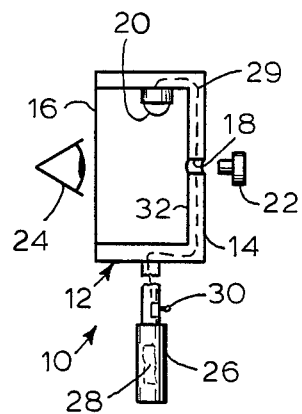
FIG. 1 is a schematic view of a brightness acuity tester embodying the present invention.

In general, each of the illustrated embodiments of a brightness acuity tester 10 for assessing human functional visual acuity in bright light conditions as well as to test for recovery of visual acuity after photostressing the retina comprises a device 12, closed as at 14 in one direction and being open as at 16 in a diametrically opposed direction, an aperture 18 provided in the device 12 in the closed direction 14, a source of illumination 20 mounted within the device 12, and a plug member 22 designed removably to be mounted within the aperture 18 to seal the same.

When the device 12 is to be used for assessing human functional visual acuity in bright light conditions, the plug 22 is removed from the aperture 18. With the open 16 side of the device 12 designed to fit about the eye 24 of a person being tested, the brightness acuity tester 10 simulates bright light outdoor conditions and yields visual acuity measurements similar to those that would be measured in direct sunlight. Thus, the resultant measurement is a measure of functional outdoor acuity. First, the patient vision is measured in the standard manner and with the best correction. With the best correction in place and the other eye occluded, the brightness acuity tester 10 is first used, with the source of illumination 20 being turned "off," by being held by the patient adjacent his eye 24 so that he is able to view an eye chart, not shown, through the aperture 18. Then, the source of illumination 20 is turned "on" and the patient is allowed a few seconds (about 5 to 10 seconds, on the average) for his eye 24 to adapt to the bright light conditions. His functional visual acuity in the eye 24 is then measured by having the patient start reading the largest letters, usually the 20/200 letters, and working his way to smaller letters. The measurement can reveal one of three possible conditions: 1/ a reduction in acuity; 2/ no change in acuity; or 3/ an improvement in acuity. With a measurement indicating a reduction in acuity, the patient's outdoor functional vision is less than that measured in the standard refracting lane.

Media opacities, such as corneal scars, cataracts, posterior capsular opacification or central vitreous floaters, are the probable cause of the impairment in acuity. With a measurement indicating a no change in acuity, the acuity measured in the standard refracting lane is an accurate index of the patient's outdoor functional visual acuity. Some patients actually show an improvement in their functional visual acuity in bright outdoor conditions. Such improved measurement indicating an increase in functional visual acuity primarily is due to the "pinhole effect" brought about by the pupil constricting in bright light conditions. The pinhole effect implies either a residual refractive error or an opacity or irregularity which is not central and is less significant when the pupil is constricted. Clinical examples manifesting improved functional visual acuity measurements include: residual refractive error, irregular astigmatism, paracentral corneal scars, non-central cortical cataracts, eccentric opacification of the posterior capsule and radial keratotomy.

When the device 12 is to be used to test for recovery of visual acuity after photostressing the retina, the plug member 22 is remounted within the aperture 18 so as seal the same. With the aperture 18 closed and the device 12 held adjacent and about the eye 24 of the patient, the brightness acuity tester 10, with the source of illumination 20 being turned "on," provides a hemispherical light source which uniformly subjects the entire macular and paramacular region of the eye 24 to photostress with a consistent brightness. The object of the test is to measure the time it takes for the eye 24 to return to normal, i.e., to within two lines of the initial visual acuity, after it has been photostressed for a prescribed minimum period of time, usually about ten to fifteen seconds. Photostress testing is particularly helpful in patients in whom cystoid macular edema is suspected following intraocular surgery. The average normal recovery time is under thirty seconds. A recovery time of between about thirty to about sixty seconds, known as a marginal prolonged recovery, suggests a possible maculopathy. A prolongation in the recovery time incriminates the macula and serves to eliminate other complicating factors, including irregular astigmatism, early capsular opacification and optic nerve disease. A prolongation in recovery time beyond sixty seconds is abnormal and signals maculopathy.

The source of illumination 20 can comprise any source of radiation, including an incandescent lamp, a light emitting diode, a fluorescent tube, and the like. Further, the source of illumination 20 can have a single preferred intensity equivalent to direct sunlight reflected, for example, from a concrete sidewalk or a sandy beach, and measuring 2,500 ft. lamberts (L). A lambert (L) is a unit of luminance (i.e., photometric brightness) that is equal to 1/ candela per square centimeter or to the uniform luminance of a perfectly diffusing surface emitting or reflecting light at the rate of one lumen per square centimeter. The luminous intensity of the source of illumination 20 preferably is varied and variable between a High, Medium and Low setting. The High setting is then represented by the just described single preferred intensity measuring about 2,500 ft. lamberts. Medium setting preferably is representative of illumination produced by indirect sunlight shining on a cloudy day and being reflected from a concrete sidewalk or sand. Such Medium setting is about one half of the High setting, measuring about 1,250 ft. lamberts. The Low setting is intended to simulate the average illumination generated by overhead fluorescent lights in commercial settings, such as may be encountered in a department store, a hospital, or the like. The Low setting is set at a luminous intensity measuring about 200 ft. lamberts. The Medium and Low settings primarily are used when a severely photophobic patient is unable to tolerate the High setting, or to simulate lower light level conditions described by a patient. For example, the patient may indicate to the tester that his observed vision deteriorates on overcast days or when shopping in a department store.

Preferably, the device 12 is hand-held and therefore is provided with a convenient handle 26. Preferably, the handle 26 accommodates a power source 28, comprising one or more replaceable batteries. In the alternative, the handle 26 will carry a pair of electrical wires 29 and a plug (not shown), by which electrical contact between an external power source (not shown) and the source of illuminator 20 in the device 12 is effected. A conveniently placed switch 30 is provided, either on the handle 26 itself, as shown in FIG. 1, or on the device 12, by which an operator can turn the source of illumination 20 on or off. Preferably, the source of illumination 20 is a wide spectral output lamp, best representing the bright light conditions out-of-doors. If desired, such as for special testing, the source of illumination 20 can comprise a lamp with a narrow band of wavelengths. The same effect also can be achieved by having filters mounted adjacent the source of illumination 20 with wide or narrow spectral output range, for special uses.

The device 12 may be angular, as shown in FIG. 1, and it may be formed of any materials, be it metal, plastic, or a combination of metal and plastic, provided that its inner surface 32 is a diffusely reflecting surface, which when lit, presents an extended white illuminated filed of view to the patient's eye 24.

Figure 2:
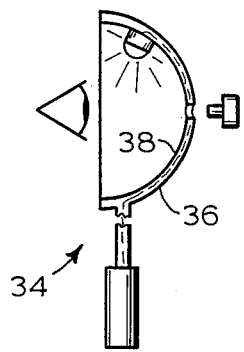
Figure 3:
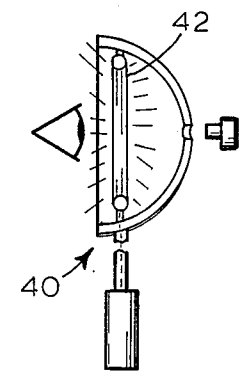
Figure 4:
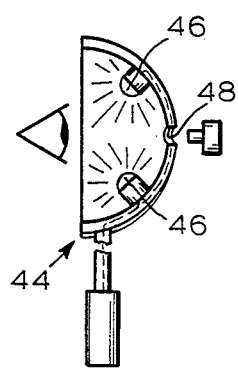
Figure 5:
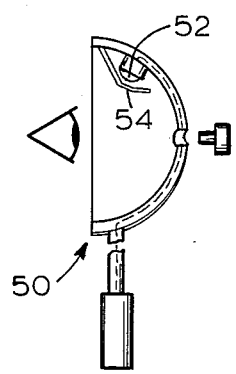
Figure 6:
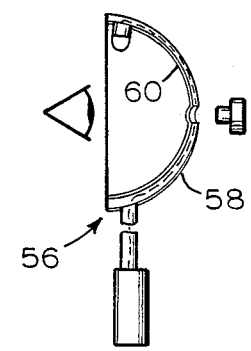
Figure 7:
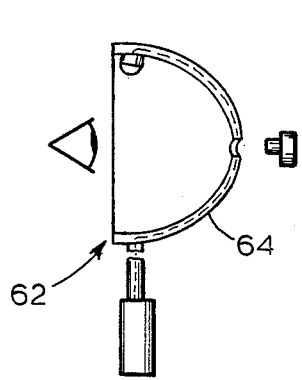
Figure 8:
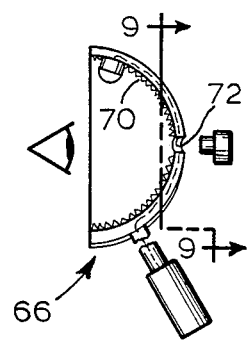
Figure 9A:
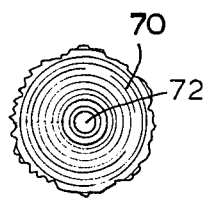
FIG. 9A is a fragmentary elevation of the brightness acuity tester of FIG. 8 and taken in the direction of the arrows 9—9.
Figure 9C:
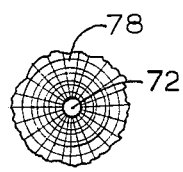
FIGS. 9B, 9C and 9D are views similar to FIG. 9A but showing variations thereof.
Figure 9B:
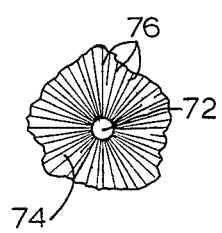
Figure 9D:
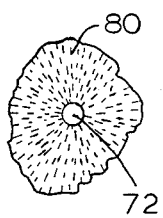

Various embodiments of the brightness acuity tester according to the invention are illustrated in FIGS. 2-8. In FIG. 2, a brightness acuity tester 34 is depicted comprising a device 36, which is a hemispherical reflector, also featuring a diffusely reflecting surface 38 on its inside. In all other respects, the tester 34 is similar to the one 10 shown in and described with reference to FIG. 1. In FIG. 3, a brightness acuity tester 40 is shown in which a source of illumination 42 comprises a circular fluorescent tube to provide a ring of illumination. In all other respects, the tester 40 is like the one 34 shown in FIG. 2. In FIG. 4 there is shown a brightness acuity tester 44 which features as its source of illumination a plurality of lamps 46 circumferentially mounted about the aperture 48. In all other aspects, the tester 44 is like the one 34 shown in FIG. 2. In FIG. 5, a brightness acuity tester 50 is illustrated with a wide spectral output lamp 52, having a filter 54. In all other respects, the tester 50 is like the one 34 shown in FIG. 2. In FIG. 6, there is shown a brightness acuity tester 56 in which the hemispherical device 58 is provided on its inner surface with a coating 60 of diffusely reflecting white paint. The coating 60 is designed so that the device 58 selectively reflects different colors, representing various wavelengths, depending on the specific coating 60 employed. In all other respects, the tester 56 is like the one 34 shown in FIG. 2. In FIG. 7, there is shown a brightness acuity tester 62, which features a device 64 shaped like a conical surface. In all other respects, the tester 62 is like the one shown in FIG. 2. And in FIG. 8, there is shown a brightness acuity tester 66 in which the inside surface of the hemispherical device 68 is a grooved surface 70, comprising a plurality of grooves formed concentric about the central viewing aperture 72. FIG. 9A is a fragmentary elevational view of the brightness acuity tester 66 and taken in the direction of the arrows 9—9 in FIG. 8. FIGS. 9B, 9C and 9D are views similar to FIG. 9A but showing variations thereof. Specifically, in FIG. 9B, a grooved surface 74 is depicted featuring a plurality of radial grooves 76 emanating as spokes from the central viewing aperture 72. FIG. 9C illustrates a grooved surface 78 which is a combination of concentric and radial grooves; whereas FIG. 9D illustrates a plurality of random grooves 80 formed on the inside surface of the hemispherical device. It is to be understood that in each instance, these respective grooves are very small and shallow. They are intended to produce a diffusely reflecting surface on the inside of the hemispherical device.

As evident from the above, the device, be it angular as in FIG. 1, hemispherical as in FIGS. 2-6 and 8, or conical as in FIG. 7, can be formed of any suitable materials, such as plastic, metal, wood or a combination thereof, provided always that its inner reflecting surface is a diffusely reflecting surface. Such a diffusely reflecting surface can be achieved by a coating or paint, with the appropriate pigmentation, or by a grooved surface in an otherwise highly polished surface.

Figure 10:
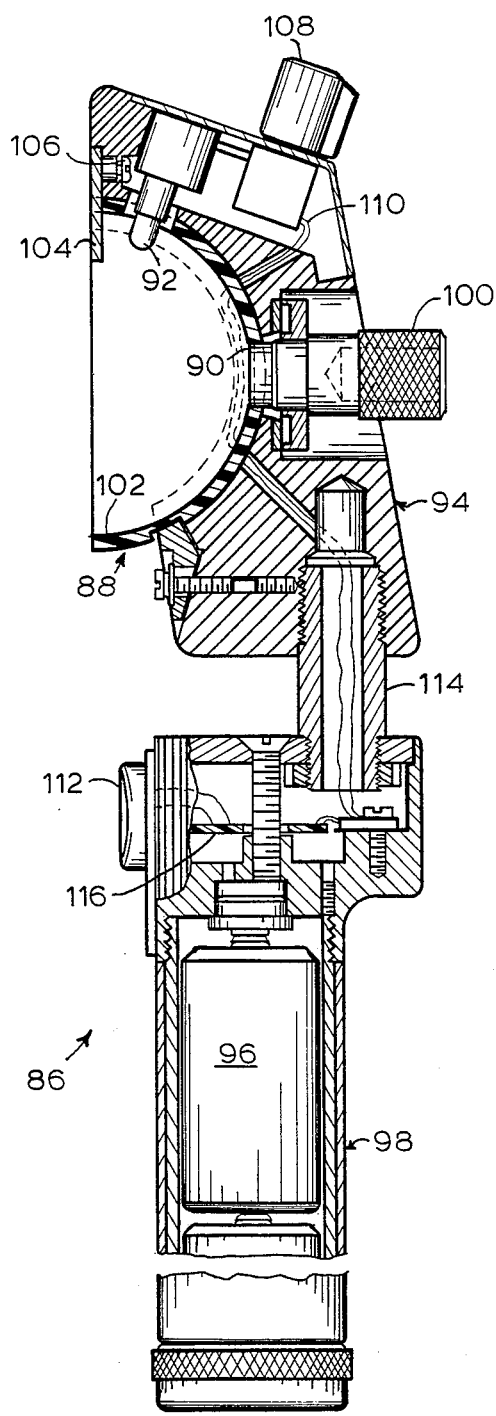
FIG. 10 is a side elevation and partly in section of a brightness acuity tester constructed in accordance with the present invention.

In FIG. 10 is illustrated, in side elevation and partly in section, a brightness acuity tester 86 constructed in accordance with the invention. Tester 86 comprises a device 88, constructed as a hemispherical reflector, an aperture 90 formed centrally therein, a source of illumination 92 mounted in the device 88 and with its filament slightly jutting into the device, all contained within a housing 94, and a power source 96 in the form of a battery pack replaceably disposed within a suitable handle 98. A plug 100 is shown in its position within the aperture 90, sealing the same. The plug 100 is conveniently removed from the aperture 90 by pulling on its knurled end. The hemispherical reflector device 88, illustrated as made of a plastic material, is formed with a smooth inside surface 102, preferably coated with a diffusely reflecting white paint. A shield plate 104 preferably is secured to the top front of the housing 94 by a pair of screws 106. The shield plate 104 is designed, if desired, to prevent the lamp 92 from shining directly into a patient's eye during testing. An intensity control knob 108 is mounted in the top of the housing 94 and in electrical contact with the lamp 92. The knob 108 is provided with three operative settings, respectively marked (not shown) at the top of the housing 94 along an arc of angular displacement of and adjacent to the knob 108 with the legend: LOW, MEDIUM and HIGH. An electrical wire 110 connects the lamp 92 to the battery pack 94 in the handle 98 via an on-off switch 112 in the form of a pushbutton conveniently located near the top front of the handle 98. A suitable connecting member 114 connects the housing 94 to the handle 98. While in FIG. 10, this connection is shown to be straight, the connection between housing 94 and handle 98 can be made at an angle, as illustrated in FIG. 8. The angle can vary from about 0 to about 20 degrees. Such an angular connection facilitates the spherical reflector 88 being placed closely adjacent to the eye of a patient, regardless of a patient's facial configuration, for example, prominent cheek bones.

Since it is desirable that the voltage level produced by the power source 96 and reaching the lamp 92 be constant in each of the three operative settings, lest the intensity of illumination generated by the lamp 92 fluctuate, a voltage regulator circuit 116 in the form of a printed-circuit board, is mounted in the upper end of the handle 98 and electircally connected between the power source 96 and the lamp 92.

Figure 11:
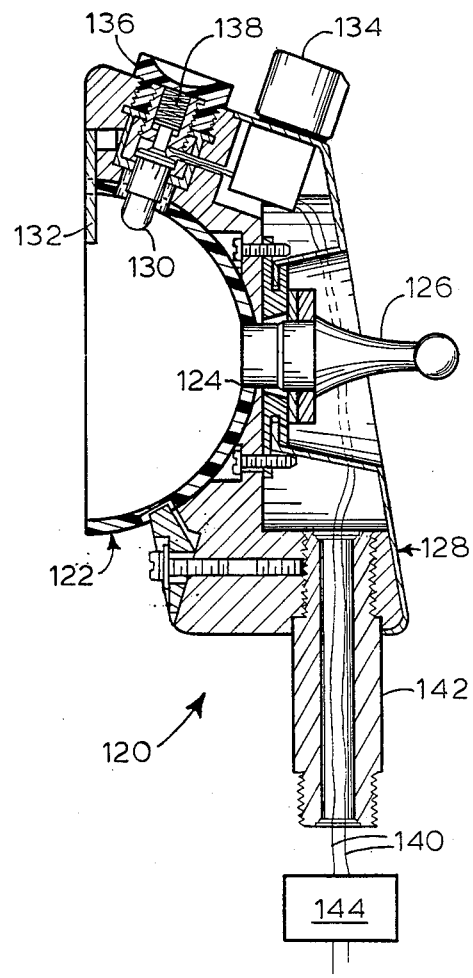
FIG. 11 is a fragmentary view, similar to FIG. 10, but showing a variation thereof.

In FIG. 11, there is illustrated a fragmentary view of a brightness acuity tester 120, i.e., without a handle, and also in side elevation and partly in section. Tester 120 comprises a hemispherical reflector device 122 having a central aperture 124, shown being sealed by a plug 126, somewhat differently mounted within a housing 128, a lamp 130, a shield plate 132, an intensity control knob 134, and a flexible pushbutton type switch 136 operatively mounted adjacent the lamp 130. A spring 138 is disposed immediately below the flexible switch 136 and provides the switch 136 with two operative states for the lamp 92: one being "off" and the second being "on." A suitable pair of wires 140 connects the lamp 130, via a connecting member 142, an A.C. adapter 144 and a handle (not shown in FIG. 11) to a conventional electrical plug, not shown. The plug is then placed within an electrical socket found in any household and connecting to conventional 115 V.A.C. power.

Thus it has been shown and described a brightness acuity tester for assessing functional visual acuity in bright light conditions and to test for recovery of visual acuity after photostressing the retina, which tester satisfies the objects and advantages set forth above.

Since certain changes may be made in the present disclosure without departing from the scope of the present invention, it is intended that all matter described in the foregoing specification or shown in the accompanying drawings, be interpreted in an illustrative and not in a limiting sense.

What is claimed is:

1. A brightness acuity tester comprising:
   (a) a portable device closed in one direction and open in a diametrically opposed direction; the periphery of said opening being sized such that the periphery of the opening is closely adjacent the eye;
   (b) said device provided with a handle;
   (c) an aperture provided in said device in said closed direction;
   (d) a plug member designed removably to be mounted within said aperture;
   (e) a source of illumination mounted within said device; and
   (f) a power source coupled to said source of illumination.

2. The brightness acuity tester of claim 1 wherein said source of illumination is a wide spectral output lamp and further including a filter mounted adjacent said lamp.

3. The brightness acuity tester of claim 1 wherein said source of illumination is an annular lamp peripherally mounted within said device.

4. The brightness acuity tester of claim 1 wherein said source of illumination comprises a plurality of lamps mounted on the inside of said device and about said aperture.

5. The brightness acuity tester of claim 1 wherein said device is a reflector having a diffusely reflecting surface, and further including a switch to control the coupling of said power source to said source of illumination.

6. The brightness acuity tester of claim 1 wherein said device is a reflector that is coated.

7. A brightness acuity tester comprising:

(a) a device closed in one direction and open in a diametrically opposed direction;
(b) an aperture provided in said device in said closed direction; and
(c) a source of illumination mounted within said device;
(d) said device being a reflector provided with a grooved surface.

8. The brightness acuity tester of claim 7 wherein said grooved surface is formed by a plurality of parallel spaced circular grooves concentric about said aperture.

9. The brightness acuity tester of claim 7 wherein said grooved surface is formed by a plurality of grooves radially projecting from said aperture.

10. The brightness acuity tester of claim 7 wherein said grooved surface is formed by a combination of a plurality of parallel spaced circular grooves concentric about said aperture and a plurality of grooves radially projecting from said aperture and intersecting said plurality of circular grooves.

11. The brightness acuity tester of claim 7 wherein said grooved surface is formed by a plurality of random grooves on the inside of said reflector.

12. The brightness acuity tester of claim 1 wherein said device is a reflector that is a conically shaped surface.

13. The brightness acuity tester of claim 1 wherein said handle is formed at an angle, and wherein said angle is from about 0 to about 20 degrees.

14. The brightness acuity tester of claim 1 further including means to vary the intensity of illumination provided by said source of illumination, means to power said source of illumination, and means interposed between said last means and said intensity varying means to maintain the selected intensity of illumination provided by said source of illumination constant despite variations in said means to power said source of illumination.

15. The brightness acuity tester of claim 14 wherein said means to power said source of illumination is a battery.

16. The brightness acuity tester of claim 14 wherein said means to power said source of illumination includes an A.C. adapter and wires coupling said power source to said source of illumination.

17. A brightness acuity tester comprising:
(a) a portable device closed in one direction and open in a diametrically opposed direction; the periphery of said opening being sized such that the periphery of the opening is closely adjacent the eye;
(b) said device being a reflector and provided with a handle;
(c) an aperture provided in said device in said closed direction and designed for said eye to view a vision testing target therethrough;
(d) a source of illumination mounted within said device; and
(e) a power source coupled to said source of illumination.

18. The brightness acuity tester of claim 17 wherein said reflector is provided with a diffusely reflecting surface.

19. The brightness acuity tester of claim 18 wherein said handle is formed at an angle, and wherein said angle is from about 0 to about 20 degrees.

20. The brightness acuity tester of claim 17 further including means to vary the intensity of illumination provided by said source of illumination, means to power said source of illumination, and means interposed between said last means and said intensity varying means to maintain the selected intensity of illumination provided by said source of illumination constant despite variations in said means to power said source of illumination.

21. The brightness acuity tester of claim 20 wherein said means to power said source of illumination is a battery.

22. The brightness acuity tester of claim 20 wherein said means to power said source of illumination includes an A.C. adapter and wires coupling said power source to said source of illumination.

* * * * *